United States Patent [19]

Kühle et al.

[11] Patent Number: 4,496,575

[45] Date of Patent: Jan. 29, 1985

[54] FUNGICIDAL N-SULPHENYLATED HYDANTOINS

[75] Inventors: Engelbert Kühle, Bergisch-Gladbach; Wilhelm Brandes, Leichlingen; Hans-Jürgen Rosslenbroich, Langenfeld; Erich Klauke, Odenthal, all of Fed. Rep. of Germany

[73] Assignee: Bayer Aktiengesellschaft, Leverkusen, Fed. Rep. of Germany

[21] Appl. No.: 501,034

[22] Filed: Jun. 3, 1983

[30] Foreign Application Priority Data

Jun. 16, 1982 [DE] Fed. Rep. of Germany ....... 3222523

[51] Int. Cl.$^3$ .................... A01N 43/50; C07D 233/82

[52] U.S. Cl. .................................... 514/390; 548/311; 548/314

[58] Field of Search ..................... 548/311; 424/273 R

[56] References Cited

U.S. PATENT DOCUMENTS 3,178,447 4/1965 Kohn .................................. 548/311

3,960,883 6/1976 Hubele ............................... 548/311

FOREIGN PATENT DOCUMENTS 1168914 4/1964 Fed. Rep. of Germany ...... 548/311

2658270 6/1977 Fed. Rep. of Germany ...... 548/311

2722035 11/1978 Fed. Rep. of Germany ...... 548/311

*Primary Examiner*—Richard A. Schwartz

*Attorney, Agent, or Firm*—Sprung, Horn, Kramer & Woods

[57] ABSTRACT

N-Sulphenylated hydantoins of the formula

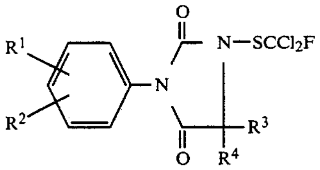

in which $R^1$ is trihalogenomethoxy or trihalogenomethylmercapto, $R^2$ is hydrogen, nitro or halogen, and $R^3$ and $R^4$ each independently is hydrogen or alkyl, or, together with the ring carbon atom at which they are located, form a five-membered or six-membered cycloalkyl radical, which possess fungicidal activity.

11 Claims, No Drawings

FUNGICIDAL N-SULPHENYLATED HYDANTOINS

The invention relates to new N-sulphenylated hydantoins, a process for their preparation and their use as pest-combating agents.

It is already known that certain N-dichlorofluoromethanesulphenyl-hydantoins can be used as fungicides in agriculture (see U.S. Pat. No. 3,960,883). Furthermore, heavy metal salts of ethylene-1,2-bis-dithiocarbamic acid, in particular zinc ethylene-1,2-bis-dithiocarbamate, have long been in use in agriculture and horticulture for combating phytopathogenic fungi (see R. Wegler, "Chemie der Pflanzenschutz- und Schädlingsbekämpfungsmittel" [Chemistry of plant protection agents and pest-combating-agents], volume 2, page 65, Springer Verlag Berlin/Heidelberg/New York (1970)).

New N-dichlorofluoromethanesulphenylhydantoins of the formula

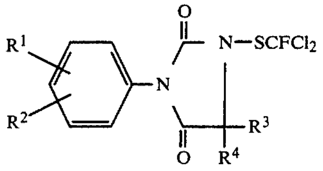

(I)

in which $R^1$ represents trihalogenomethoxy or trihalogenomethylmercapto, $R^2$ represents hydrogen, nitro or halogen and $R^3$ and $R^4$ are identical or different and represent hydrogen or alkyl, or, together with the ring carbon, form a five-membered or six-membered cycloalkyl radical, have now been provided.

The new N-sulphenylated hydantoins of the formula (I)

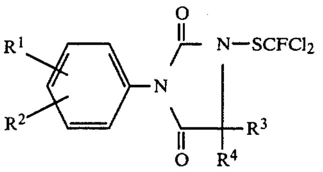

(I)

in which $R^1$ represents trihalogenomethoxy or trihalogenomethylmercapto, $R^2$ represents hydrogen, nitro or halogen and $R^3$ and $R^4$ are identical or different and represent halogen or alkyl, or, together with the ring carbon at which they are located, form a five-membered or six-membered cycloalkyl radical, are obtained when a hydantoin of the formula

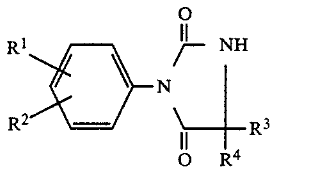

(II)

in which $R^1$, $R^2$, $R^3$ and $R^4$ have the meaning given above, is reacted with a dichlorofluoromethanesulphenyl halide of the formula $$X—SCCl_2F \quad (III)$$

in which

X represents halogen, if appropriate in the presence of an acid-binding agent and of a diluent.

The new N-sulphenylated hydantoins of the formula (I) possess fungicidal properties. Surprisingly, they exhibit a superior action compared with the known compounds. They thus represent an enrichment of the art.

Formula (I) gives a definition of the N-sulphenylated hydantoins according to the invention. In this formula $R^1$ preferably represents trichloromethoxy, trifluoromethoxy, trichloromethylmercapto, trifluoromethylmercapto, difluorochloromethoxy, fluorodichloromethoxy, difluorochloromethylmercapto or fluorodichloromethylmercapto, $R^2$ preferably represents hydrogen, nitro or chlorine, and $R^3$ and $R^4$ are identical or different and represent hydrogen or lower alkyl having 1 to 4 carbon atoms, or, together with the ring carbon atom at which they are located, represent cyclopentyl or cyclohexyl.

Particularly preferred compounds of the formula (I) are those in which $R^1$ represents trichloromethoxy, trifluoromethoxy, trichloromethylmercapto, trifluoromethylmercapto, difluorochloromethoxy, fluorodichloromethoxy, difluorochloromethylmercapto or fluorodichloromethylmercapto, $R^2$ represents hydrogen or chlorine, and $R^3$ and $R^4$ are identical and represent hydrogen or lower alkyl having 1 to 3 carbon atoms, such as methyl, ethyl, iso-propyl and n-propyl, or, together with the ring carbon atom, form a cyclopentyl or cyclohexyl radical.

If, for example, 3-(4-trifluoromethoxyphenyl)-hydantoin and dichlorofluoromethanesulphenyl chloride are used as starting materials for the preparation of the compounds according to the invention, the course of the reaction can be represented by the following equation:

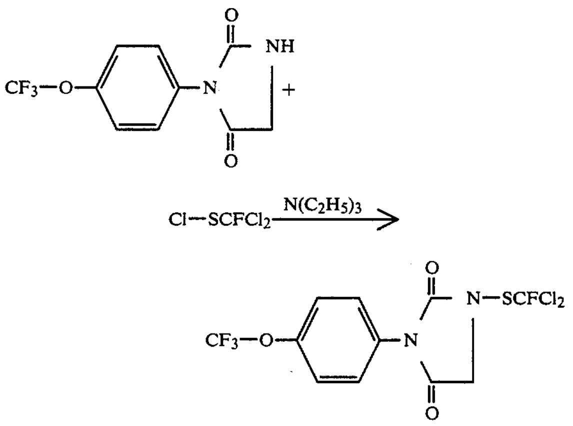

Formula (III) gives a definition of the dichlorofluoromethanesulphenyl halides to be used as starting materials in carrying out the process according to the invention. In this formula (III), X represents halogen, such as chlorine or bromine, preferably chlorine.

The dichlorofluoromethanesulphenyl halides are known, and can be prepared by known processes [see, for example, Angew. Chemie 76, page 807 (1964)].

Formula (II) gives a definition of the hydantoins additionally to be used as starting materials. In this formula (II), $R^1$ to $R^4$ represent the radicals which have already been mentioned in connection with the description of the substances according to the invention of the formula (I), for these substituents.

The majority of these hydantoins of the formula (II) are known, and can be prepared by known processes, thus, for example, by reacting the corresponding phenylisocyanates with aminoacetic acid, and subsequently cyclizing the product with elimination of water

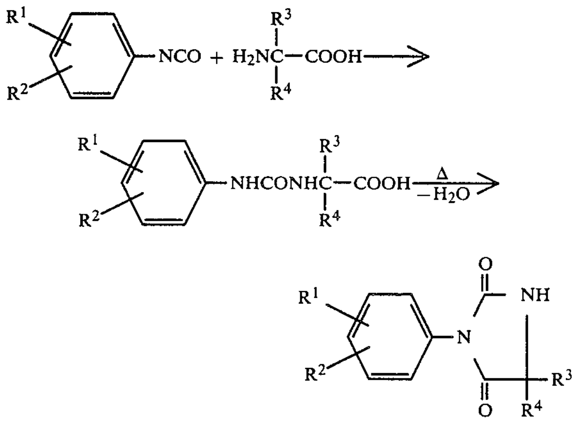

or by the addition reaction of appropriate aminoacetonitriles with isocyanates and subsequent cyclization and hydrolysis of the imino radical, for example

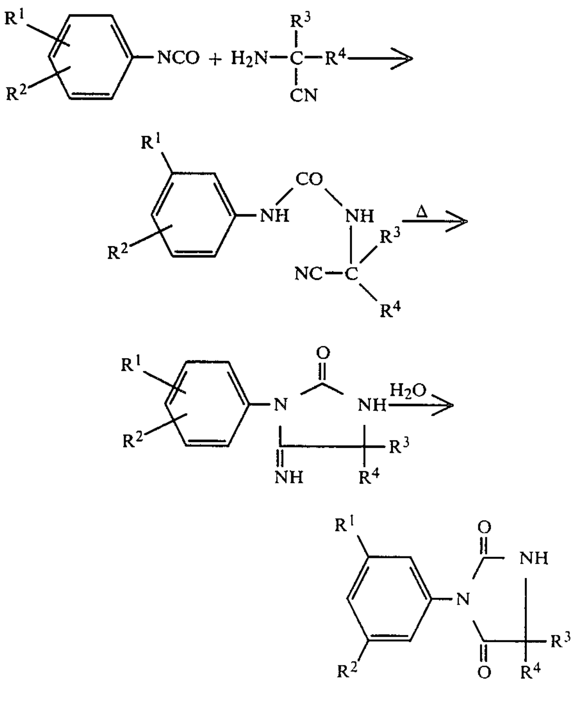

(see Chem. Abstracts 55, 27277 h (1961).

In carrying out the process, suitable diluents are all inert organic solvents. These preferably include hydrocarbons, such as toluene, chlorohydrocarbons, such as chlorobenzene, and ethers, such as dioxane. However, the reaction can also be carried out in water.

Tertiary amines and alkali metal hydroxides or alkali metal carbonates, such as sodium hydroxides or sodium carbonate, can be used as acid-binding agents.

The reaction temperatures can be varied within a relatively wide range. In general, the reaction is carried out at between about 0° C. and 100° C., preferably at 20° to 50° C.

In carrying out the reaction, 1 mol of trihalogenomethanesulphenyl halide is employed per mol of the appropriate hydantoin. A small excess of up to 3% of the sulphenyl halide does not have an adverse effect. The isolation of the end products of the formula (I) is effected in a generally customary manner.

The active compounds according to the invention exhibit a powerful microbicidal action and can be employed in practice for combating undesired microorganisms. The active compounds are suitable for use as pest-combating agents.

Thus, for example, fungicidal agents are employed in plant protection for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds, with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglcol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

PREPARATION EXAMPLES

EXAMPLE 1

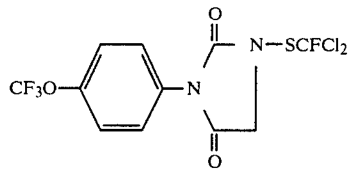

18.2 g (0.07 mol) of 3-(4-trifluoromethoxyphenyl)-hydantoin are dissolved in 100 ml of dioxane, with the addition of 12.5 g (0.074 mol) of dichlorofluoromethanesulphenyl chloride. 8 g (0.079 mol) of triethylamine are added dropwise to this solution. The temperature increases to 53° C. during this procedure. The mixture is stirred for about 15 minutes, and the product is precipitated by the addition of water. 11 g (40% of theory) of 1-dichlorofluoromethylmercapto-3-(4-trifluoromethoxy-phenyl)-hydantoin of melting point 153°-156° C. are obtained.

The following compounds of the formula I

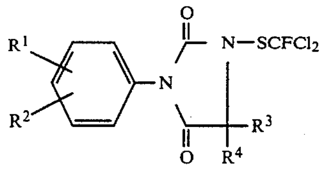

(I)

are obtained in a similar manner:

| Example No. | $R^1$ | $R^2$ | $R^3$ | $R^4$ | Melting Point (°C.) |
|---|---|---|---|---|---|
| 2 | 4-$F_3$CO— | H | $CH_3$ | $CH_3$ | 85 |
| 3 | 4-Cl$F_2$C—O— | H | H | H | 152 |
| 4 | 4-Cl$F_2$—C—O— | H | $CH_3$ | $CH_3$ | 88 |
| 5 | 4-$F_3$C—S— | H | H | H | 150 |
| 6 | 4-$F_3$C—S— | H | $CH_3$ | $CH_3$ | 94 |
| 7 | 4-$F_3$C—O— | 3-Cl | H | H | 98 |
| 8 | 4-$F_3$C—O— | 3-Cl | $CH_3$ | $CH_3$ | 82 |
| 9 | 4-Cl$F_2$C—O— | 3-Cl | H | H | 85 |
| 10 | 4-Cl$F_2$C—S— | 3-Cl | H | H | 87 |

PREPARATION EXAMPLES OF THE STARTING COMPOUNDS

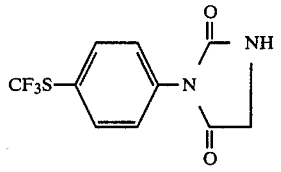

7.5 g (0.1 mol) of aminoacetic acid are dissolved in 100 ml of water, with the addition of 4 g (0.1 mol) of sodium hydroxide. 21.9 g (0.1 mol) of 4-trifluoromethylmercaptophenyl isocyanate, dissolved in 50 ml of acetone, are added dropwise to the above solution. The mixture is stirred for about 15 minutes, and acidified with hydrochloric acid. During this procedure, 30 g of the adduct of melting point 182°-184° C. are precipitated.

After drying, 4-trifluoromethylmercaptophenylcarbamoyl-aminoacetic acid is heated in a water separator for about 30 minutes, with the addition of 2 ml of concentrated sulphuric acid in 350 ml of xylene. After the solvent has been distilled off and after the residue has been stirred with water, 21 g of 3-(4-trifluoromethylmercaptophenyl)-hydantoin of melting point 117°-120° C. are obtained.

The following compounds of the formula (II)

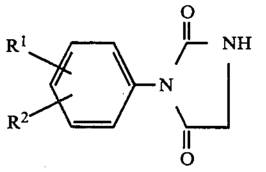
(II)

are obtained in the same manner:

| Example | $R^1$ | $R^2$ | Melting Point (°C.) |
|---|---|---|---|
| b | 4-$CF_3$—O— | H | 140 |
| c | 4-$CF_2Cl$—O— | H | 137 |
| d | 4-$CF_3$—O— | 3-Cl | 120 |
| e | 4-$CF_2Cl$—S— | 3-Cl | 137 |
| Example f | 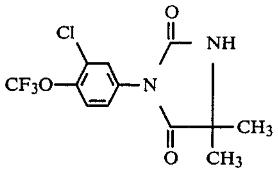 | | |

6.5 g (0.077 mol) of α-aminoisobutyronitrile are added dropwise to a solution of 17.1 g (0.072 mol) of 3-chloro-4-trifluoromethoxyphenyl isocyanate in 100 ml of acetone. The temperature increases to about 45° C. during this procedure. After the reaction has ceased, the solvent is evaporated off in vacuo, and the residue is then boiled for 1 hour with 80 ml of semi-concentrated hydrochloric acid. The 3-(3-chloro-4-trifluoromethoxyphenyl)-5,5-dimethyl-hydantoin formed during this process is recrystallized from toluene with the addition of petroleum ether. 16 g of product of melting point 104°-107° C. are obtained.

The following compounds of the formula

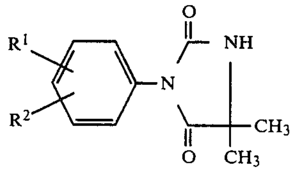

are obtained in a similar manner:

| Example | $R^1$ | $R^2$ | Melting Point (°C.) |
|---|---|---|---|
| g | 4-$CF_2Cl$—O— | 3-Cl | 134 |
| h | 4-$CF_3$—O— | H | 152 |
| i | 4-$CF_3$—S— | H | 140 |

USE EXAMPLES

The known compounds listed below are employed as comparative substances in the examples which follow:

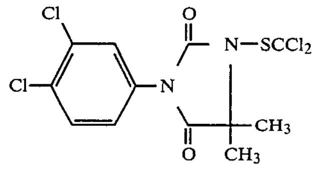
(A)

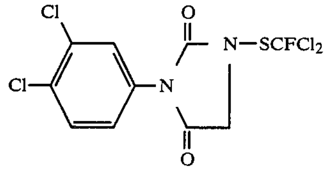
(B)

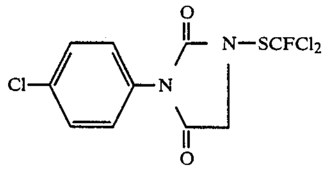
(C)

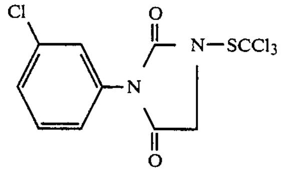
(D)

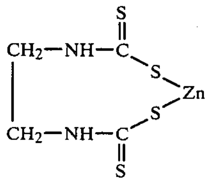
(E)

EXAMPLE A

Phytophthora Test (tomato)/protective

Solvent: 4.7 parts by weight of acetone

Emulsifier: 0.3 parts by weight of alkylaryl polycycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compounds according to the following preparation examples: 5, 3, 9, 1, 2, 4 and 7.

EXAMPLE B

Leptosphaeria nodorum test (wheat)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptosphaeria nodorum. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 7, 4, 2, 1, 10, 9, 3 and 5.

EXAMPLE C

Pyricularia test (rice)/protective

Solvent: 12.5 parts by weight of acetone

Emulsifier: 0.3 parts by weight of alkylaryl polyglycol ether

To produce a suitable preparation of active compound, 1 part by weight of active compound is mixed with the stated amounts of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to the following preparation examples: 1 and 5.

EXAMPLE D

Pellicularia test (rice)

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

In this test, a clearly superior activity compared with the prior art is shown, for example, by the compounds according to the following preparation examples: 3 and 9.

It will be appreciated that the instant specification and examples are set forth by way of illustration and not limitation, and that various modifications and changes may be made without departing from the spirit and scope of the present invention.

What is claimed is:

1. An N-sulphenylated hydantoin of the formula

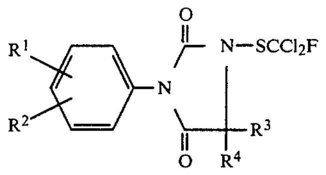

in which:

$R^1$ is trihalogenomethoxy or trihalogenomethylmercapto, $R^2$ is hydrogen, nitro or halogen, and $R^3$ and $R^4$ each independently is hydrogen or alkyl having 1 to 4 carbon atoms, or, together with the ring carbon atom at which they are located, form a five-membered or six-membered cycloalkyl radical.

2. A compound according to claim 1, in which:

$R^1$ is trichloromethoxy, trifluoromethoxy, trichloromethylmercapto, trifluoromethylmercapto, difluorochloromethoxy, fluorodichloromethoxy, difluorochloromethylmercapto or fluorodichloromethylmercapto, $R^2$ is hydrogen, nitro or chlorine, and $R^3$ and $R^4$ each independently is hydrogen or lower alkyl having 1 to 4 carbon atoms, or, together with the ring carbon atom at which they are located, form a cyclopentyl or cyclohexyl ring.

3. A compound according to claim 1, in which:

$R^1$ is trichloromethoxy, trifluoromethoxy, trichloromethylmercapto, trifluoromethylmercapto, difluorochloromethoxy, fluorodichloromethoxy, difluorochloromethylmercapto or fluorodichloromethylmercapto, $R^2$ is hydrogen or chlorine, and $R^3$ and $R^4$ each independently is hydrogen or lower alkyl having 1 to 3 carbon atoms, or, together with the ring carbon atom, form a cyclopentyl or cyclohexyl radical.

4. A compound according to claim 1, wherein such compound is 1-dichlorofluoromethylmercapto-3-(4-trifluoromethoxy-phenyl)-hydantoin of the formula

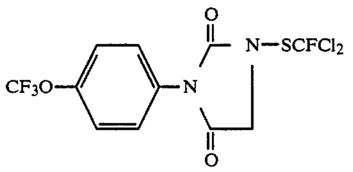

5. A compound according to claim 1, wherein such compound is 1-dichlorofluoromethylmercapto-3-(4-chlorodifluoromethoxy-phenyl)-hydantoin of the formula

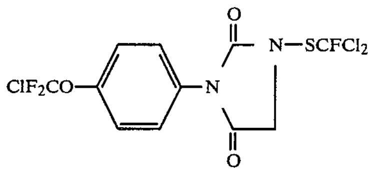

6. A compound according to claim 1, wherein such compound is 1-dichlorofluoromethylmercapto-3-(4-trifluoromethylmercapto-phenyl)-hydantoin of the formula

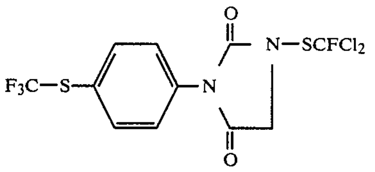

7. A compound according to claim 1, wherein such compound is 1-dichlorofluoromethylmercapto-3-(3-chloro-4-trifluoromethoxy-phenyl)-hydantoin of the formula

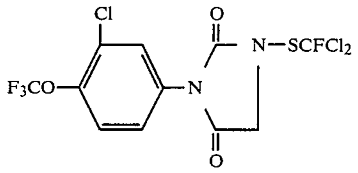

8. A compound according to claim 1, wherein such compound is 1-dichlorofluoromethylmercapto-3-(3-chloro-4-chlorodifluoromethoxy-phenyl)-hydantoin of the formula

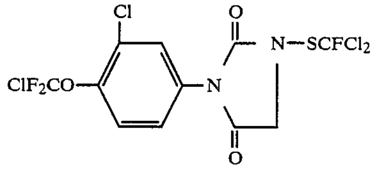

9. A fungicidal composition comprising a fungicidally effective amount of a compound according to claim 1 in admixture with a diluent.

10. A method of combating fungi which comprises administering to such fungi a fungicidally effective amount of a compound according to claim 1.

11. The method according to claim 10, wherein such compound is 1-dichlorofluoromethylmercapto-3-(4-trifluoromethoxy-phenyl)-hydantoin,
1-dichlorofluoromethylmercapto-3-(4-chlorodifluoromethoxy-phenyl)-hydantoin,
1-dichlorofluoromethylmercapto-3-(4-trifluoromethylmercapto-phenyl)-hydantoin,
1-dichlorofluoromethylmercapto-3-(3-chloro-4-trifluoromethoxy-phenyl)-hydantoin, or
1-dichlorofluoromethylmercapto-3-(3-chloro-4-chlorodifluoromethoxy-phenyl)-hydantoin.

* * * * *

UNITED STATES PATENT AND TRADEMARK OFFICE

CERTIFICATE OF CORRECTION

PATENT NO. : 4,496,575

DATED : January 29, 1985

INVENTOR(S) : Engelbert Kühle, et al

It is certified that error appears in the above-identified patent and that said Letters Patent is hereby corrected as shown below:

| | |
|---|---|
| Col. 1, line 55 | Delete "halogen" and substitute --hydrogen-- |
| Col. 3, line 15 | Insert space between "phenyl" and isocyanates" |
| Col. 6, line 51 | Insert --Example a: -- |
| Col. 8, line 3 | End of formula "(A)" delete "$-SCCl_2$" and substitute --$SCCl_3$-- |

Signed and Sealed this

*Twenty-seventh* Day of *August 1985*

[SEAL]

*Attest:*

DONALD J. QUIGG

*Attesting Officer* *Acting Commissioner of Patents and Trademarks*